US00PP22364P3

(12) United States Plant Patent
Dunne

(10) Patent No.: US PP22,364 P3
(45) Date of Patent: Dec. 20, 2011

(54) ***CISTUS* PLANT NAMED 'DUNNECIS'**

(50) Latin Name: *Cistus×hybridus*
Varietal Denomination: DUNNECIS

(76) Inventor: Kieran Dunne, Naas (IE)

( * ) Notice: Subject to any disclaimer, the term of this patent is extended or adjusted under 35 U.S.C. 154(b) by 0 days.

(21) Appl. No.: 12/806,357

(22) Filed: Aug. 10, 2010

(65) Prior Publication Data

US 2011/0047663 P1 Feb. 24, 2011

(51) Int. Cl.
*A01H 5/00* (2006.01)

(52) U.S. Cl. ..... Plt./226

(58) Field of Classification Search ..... Plt./226
See application file for complete search history.

*Primary Examiner* — Susan McCormick Ewoldt

(57) ABSTRACT

A new cultivar of *CISTUS* plant named 'DUNNECIS' that is characterized by compact clump-forming habit becoming prostrate with age, bright golden variegated foliage, and pure white saucer shaped flowers which bloom from early summer until fall. In combination these traits set 'DUNNECIS' apart from all other existing varieties of *CISTUS* known to the inventor.

4 Drawing Sheets

Genus, species: *CISTUS×hybridus*.
Varietal denomination: 'DUNNECIS'.

BACKGROUND OF THE INVENTION

This application claims the benefit of priority under 35 U.S.C. 119(f) of the application for a grant of European Community Plant Breeders Rights which was filed for the instant plant variety on Aug. 21, 2009, Application Number 2009/1560.

The present invention relates to a new and distinct cultivar of *Cistus×hybridus* (which is a synonym for *Cistus×corbariensis*) commonly known as white rock rose which is grown for use as an ornamental half-hardy shrub. The new cultivar is known botanically as *Cistus×hybridus* and will be referred to hereinafter by the cultivar name 'DUNNECIS'.

'DUNNECIS' was discovered as a naturally occurring branch sport at the inventor's nursery in County Kildare, Ireland, in 2005. The sport was found on a single plant of *Cistus×corbariensis* (species, unpatented) which the inventor was maintaining as a mother stock plant at his nursery. The inventor observed that the branch sport exhibited attractive bright golden yellow variegated foliage. The inventor removed the branch sport and was able to make four stem cuttings which the inventor rooted in 2005 and observed in 2006 for uniformity and trueness to type. During 2006, the inventor found that the rooted cuttings had produced plants which were identical in to the parent plant in all respects except for the variegation of the foliage.

The closest comparison plant known to the inventor is *CISTUS* 'Rencis' (U.S. Plant Pat. No. 20,410) which is also variegated. 'DUNNECIS' is distinguishable from 'Rencis' as follows: Whereas 'DUNNECIS' exhibits bright golden leaf margins, the leaf margins of 'Rencis' are yellow to creamy white. In addition the leaves of 'DUNNECIS' are approximately one-third smaller than the leaves of 'Rencis' and the mature habit of 'DUNNECIS' is markedly more prostrate than 'Rencis'. Whereas 'Rencis' achieves a height of approximately 1.5 meters and a spread of 1.2 meters, the mature height of 'DUNNECIS' is approximately 0.5 meters with a spread of approximately 1 meter.

The cultural requirements of 'DUNNECIS' are planting in well drained soil in full sun. Once established, plants of 'DUNNECIS' are drought tolerant and when in flower are attractive to bees and butterflies.

The first asexual reproduction of 'DUNNECIS' was conducted by the inventor in 2005 at the inventor's nursery in County Kildare, Ireland. The method used for asexual propagation was softwood cuttings. The characteristics of the new cultivar have been determined stable and are reproduced true to type in successive generations.

From 2005 until 2009, the inventor continued to build up stocks of 'DUNNECIS' at his nursery. All plants of 'DUNNECIS' remained under the inventor's control until the first sales which occurred on Jul. 8, 2009.

SUMMARY OF THE INVENTION

The following traits have been repeatedly observed and represent the characteristics of 'DUNNECIS'. These traits in combination distinguish 'DUNNECIS' from all other commercial varieties of *CISTUS* known to the inventor. 'DUNNECIS' has not been tested under all possible conditions and phenotypic differences may be observed with variations in environmental, climatic and cultural conditions, without however, any difference in genotype.

1. 'DUNNECIS' grows with a compact clump-forming habit, becoming prostrate with age.
2. After one year, a plant of 'DUNNECIS' is 30 cm in height (including the flowers) and 30 cm in diameter.
3. After four years of growth, the foliage mound of a plant of DUNNECIS is 0.5 meter in height and 1.0 meter in diameter.
4. 'DUNNECIS' bears medium green foliage with bright golden yellow margins.
5. The flowers of 'DUNNECIS' are saucer shaped and are white with a pronounced orange centre.
6. 'DUNNECIS' commences flowering in May and continues throughout summer and into fall.
7. 'DUNNECIS' is hardy to USDA Zone 9.
8. 'DUNNECIS' is drought tolerant once established.
9. 'DUNNECIS' attracts bees and butterflies.

BRIEF DESCRIPTION OF THE DRAWINGS

The accompanying color drawings illustrate the overall appearance of the new variety 'DUNNECIS' showing the colors as true as it is reasonably possible to obtain in colored reproductions of this type. Colors in the drawings may differ from the color values cited in the detailed botanical description, which accurately describe the actual colors of the new variety 'DUNNECIS'. All of the plants in the drawings were grown out of doors in County Kildare, Ireland.

The drawing labeled

The drawing labeled

The drawing labeled

The drawing labeled

Figure 1:
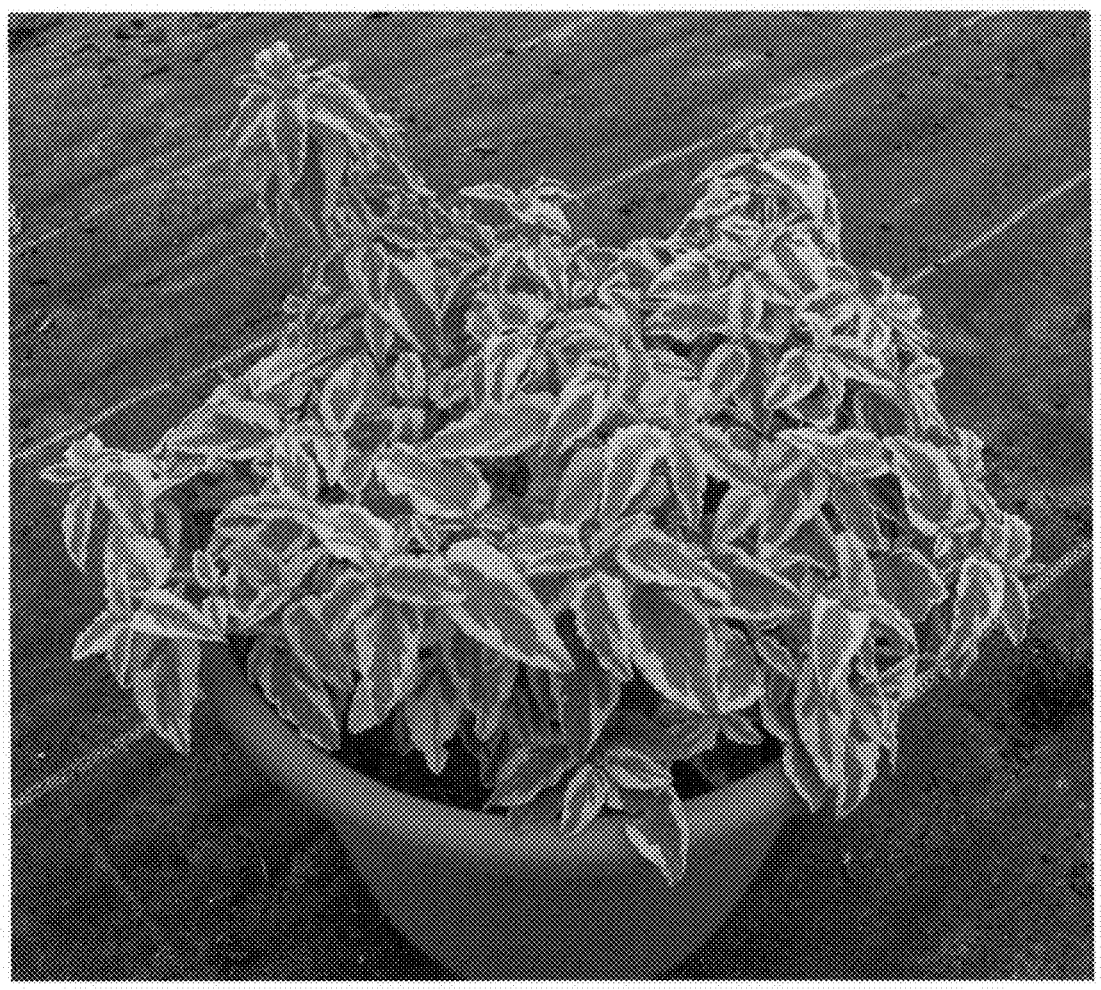
FIG. 1 depicts a one year of plant of 'DUNNECIS' which is planted in a 20 cm diameter container and is in its new spring growth and prior to flowering.
Figure 2:
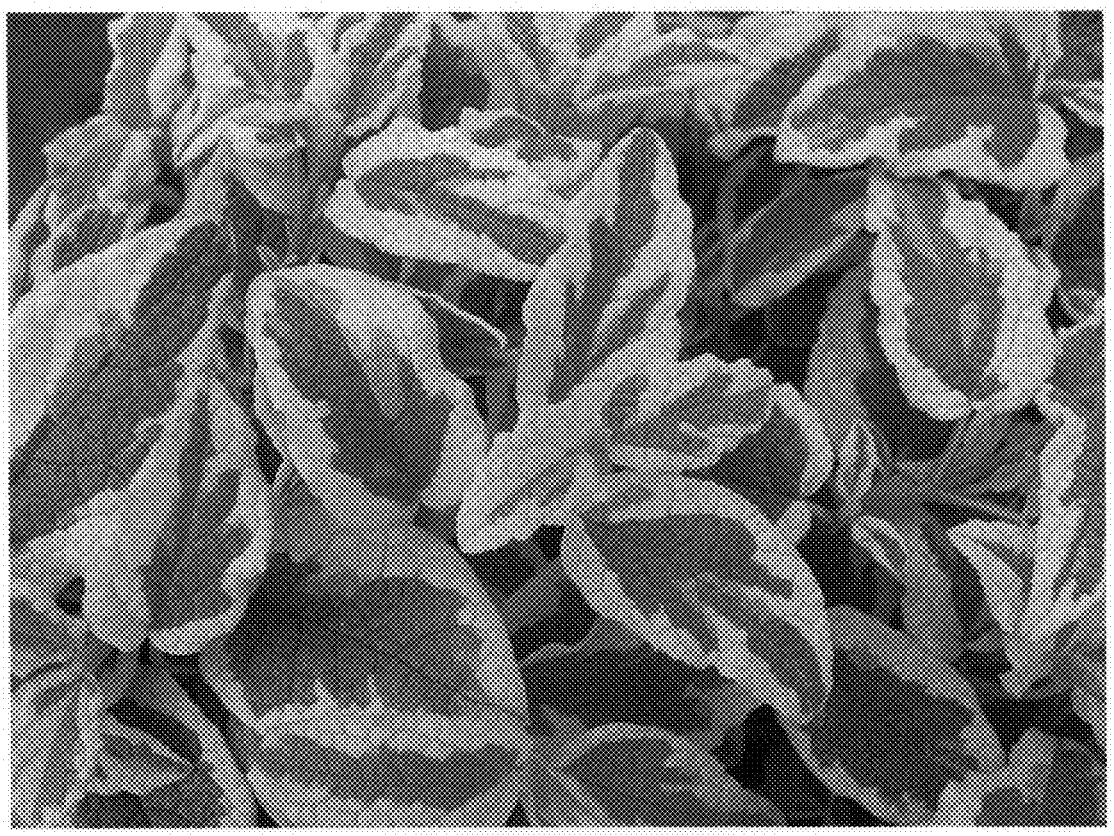
FIG. 2 depicts a close-up view of the foliage of 'DUNNECIS'. This drawing was made from a plant in spring growth although the color and variegation of 'DUNNECIS' persists through summer into fall.
Figure 3:
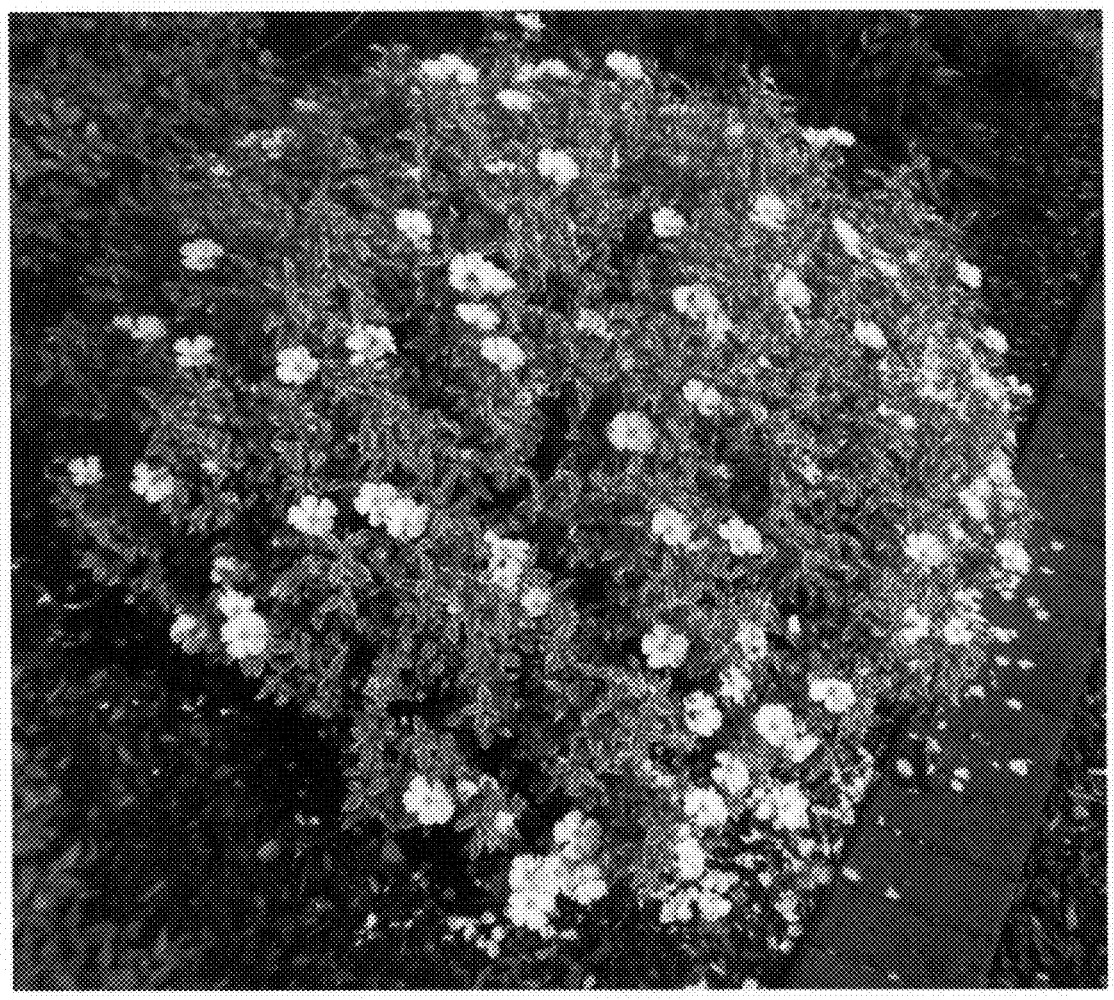
FIG. 3 depicts a mature 3 year old plant of 'DUNNECIS' which is growing in the border soil. The illustrated plant is in its mid summer flowering.
Figure 4:
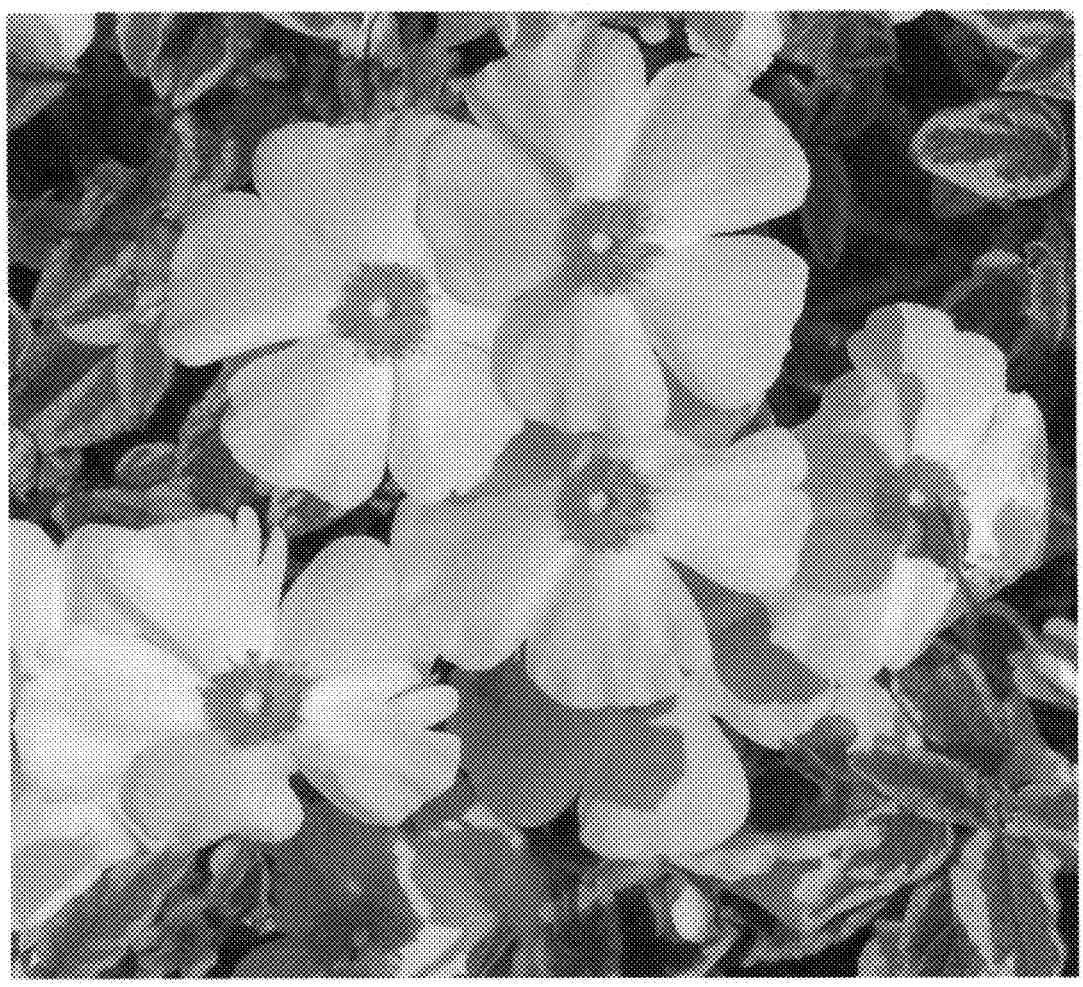
FIG. 4 depicts a close-up view of the flower of 'DUNNECIS' in summer.

The drawings were made using conventional techniques and although colors may appear different from actual colors due to light reflectance they are as accurate as possible by conventional photography.

BOTANICAL DESCRIPTION OF THE PLANT

The following is a detailed description of 'DUNNECIS'. Data was collected from one year old plants in their first season of growth, grown in 10 cm container out of doors in Santa Barbara, Calif. Additional references to the description of a mature plant have been made by the inventor using plants which are established at his nursery in County Kildare, Ireland. The color determinations are in accordance with the 2007 Fifth Edition of the Colour Chart of The Royal Horticultural Society, London, England, except where general color terms of ordinary dictionary significance are used. Growing conditions, diseases and pests are similar to that of other *CISTUS*.

Botanical classification: *CISTUS* 'DUNNECIS'.

Species: ×*hybridus*.

Commercial classification: Half-hardy shrub.

Use: Ornamental.

Cultural requirements: Plant in well drained soil in full sun.

Parentage: 'DUNNECIS' originated as a branch sport on a plant of an unknown species of *Cistus*×*corbariensis*.

Plant description:

- *Plant habit.*—Compact clump-forming, becoming prostrate when mature.
- *Dimensions.*—One year old plant: 30 cm in height (including the flowers), 30 cm in diameter. Mature (four years old) plant: 0.5 meter in height (excluding the flowers), 1.0 meter in diameter.
- *Blooming period.*—From May through summer and into fall.
- *Lastingness of an individual flower* (*on the plant*).—1- 3 days.
- *Cold hardiness.*—Hardy in U.S.D.A. Zone 9 and higher.
- *Heat tolerance.*—Tolerates full sun and 35° C. in low to moderate humidity. Does not tolerate hot and humid continental conditions.
- *Pest and diseases resistance or susceptibility.*—None known to the inventor.
- *Root description.*—Fibrous.
- *Propagation.*—Softwood stem cuttings.
- *Crop time.*—12-15 months from a cutting, in a 1 liter container.
- *Growth rate.*—Moderate.

Stem description:

- *Shape.*—Round.
- *Stem color.*—New growth 144D, maturing to 163C.
- *Stem dimensions.*—15 cm in length and 2 mm in width.
- *Stem surface.*—Smooth with sparse pubescence; hairs very fine, light gray, 1 mm-2 mm in length.
- *Internode length.*—1.0-1.5 cm.
- *Branching.*—Vigorous: lateral branches form at every node.

Foliage description:

- *Leaf shape.*—Ovate.
- *Leaf division.*—Simple.
- *Leaf base.*—Cordate.
- *Leaf apex.*—Acute.
- *Leaf fragrance.*—None.
- *Leaf venation.*—Pinnate, markedly impressed, color 191A.
- *Leaf margins.*—Denticulate and ciliate; hairs fine, light gray, 0.5 mm in length.
- *Leaf arrangement.*—Opposite.
- *Leaf attachment.*—Petiolate.
- *Leaf surface.*—Upper surface smooth; lower surface puberulent, many very fine short hairs, less than 0.1 mm in length, appear light gray to silver.
- *Leaf size.*—2.5 cm-3.5 cm in length; 1.5-1.8 cm in width.
- *Leaf variegation pattern.*—Approximately one-third to two-thirds of the leaf surface exhibits golden yellow margins which extend from 2 mm to 4 mm inward from leaf margin, except that the yellow gold margin is very narrow (less than 1 mm in width) at the leaf base and apex. The remaining green central portion of each leaf is predominantly mid-green with small gray-green patches.
- *Leaf colors* (*upper surface*).—Margin: 154B as leaf emerges, becoming 4A. Center: Predominantly 143A, with small patches 194C.
- *Leaf colors* (*lower surface*).—Margin: 154B as leaf emerges, becoming 4A. Center: Predominantly 143A, with small patches 194C.
- *Petioles.*—Dimensions: 0.4-0.6 mm in length; 1 mm in diameter. Color 144D. Surface: Smooth with sparse pubescence; hairs very fine, light gray, 1 mm-2 mm in length.

Inflorescence description:

- *Inflorescence type.*—Flowers borne singly.
- *Flower buds.*—Dimensions: Length 7 mm; diameter 3 mm. Shape: Ovate. Color: N138B. Surface: Glabrous.
- *Flowers.*—Flowers are numerous and short-lasting. A first year plant bears from 10 to 30 newly opened flowers as the season progresses. Fragrance: None. Shape: Single, saucer shaped. Dimensions: Average of 3.8 cm in diameter and 5 mm in depth.
- *Peduncles.*—Shape: Round. Dimensions: 2.0-2.5 cm in length and 1 mm in diameter. Color: 138A. Surface: Glabrous.
- *Pedicels.*—Dimensions: About 3.6 cm in length and 1 mm in diameter. Color: 138A. Surface: Glabrous.
- *Calyx and sepals.*—Calyx dimensions: 4 mm in depth and 1.3 cm in diameter. Sepals: 5, ovate, 5 mm in length and 3 mm in width. Sepal base: Apiculate.

Sepal apex: Cordate. Sepal margin: Entire. Sepal surface: Smooth. Sepal color (both surfaces): 150B to 150C with base 145A to 145B.

*Petals.*—Number: 5. Shape: Ovate. Dimensions: 7 mm in length and 5 mm in width. Base: Apiculate. Apex: Cordate. Margin: Entire. Surface: Smooth, matte, delicate. Color (both surfaces): Pure white.

*Reproductive organs.*—Pistils: 10-15, Terete but short, less than 0.5 mm in length. Styles: Less than 0.5 mm in length, color 159D. Stigmas: Clavate, color 159D. Stamens: 125-150, arranged as a shallow saucer-shaped disc. Filaments: Length 5 mm, diameter, less than 0.5 mm, color 9B. Anthers: Ovoid, basifixed, 2 mm in length, 1 mm in width, color 9B. Pollen: Moderate, color 14B.

*Fruit and seed.*—No fruit or seed production has been observed.

The invention claimed is:

1. A new and distinct cultivar of *CISTUS* plant named 'DUNNECIS' as described and illustrated herein.

* * * * *